United States Patent [19]

Hurtel et al.

[11] Patent Number: 4,851,568

[45] Date of Patent: Jul. 25, 1989

[54] PROCESS FOR THE MANUFACTURE OF DIALKYLAMINOALKYL (METH)ACRYLATES

[75] Inventors: Patrice Hurtel, St. Avold; Charles Hazan, Paris; Francois de Champs, St. Avold; Jean-Michel Pau, Toulouse, all of France

[73] Assignee: Norsolor, Paris LaDefense, France

[21] Appl. No.: 216,593

[22] Filed: Jul. 8, 1988

[30] Foreign Application Priority Data

Jul. 8, 1987 [FR] France .................. 87 09697

[51] Int. Cl.$^4$ .................................................. C07C 69/52
[52] U.S. Cl. ................................... 560/222; 560/217
[58] Field of Search ............................. 560/222, 217

[56] References Cited

U.S. PATENT DOCUMENTS

| | | | |
|---|---|---|---|
| 2,138,763 | 11/1968 | Graves | 560/222 |
| 3,714,234 | 1/1973 | White | 560/222 |
| 4,001,304 | 1/1977 | Nyi et al. | 560/222 |
| 4,009,201 | 2/1977 | Steckler et al. | 560/222 |
| 4,059,617 | 11/1977 | Foster et al. | 560/222 |
| 4,060,529 | 11/1977 | Slejko | 560/222 |
| 4,169,208 | 9/1979 | Kametani et al. | 560/222 |
| 4,202,990 | 5/1980 | Murakami et al. | 560/222 |
| 4,239,855 | 12/1980 | Zimmerman | 560/222 |
| 4,277,319 | 7/1981 | Nyi et al. | 560/222 |

FOREIGN PATENT DOCUMENTS 0118639 10/1983 European Pat. Off. .
1543279 7/1969 Fed. Rep. of Germany .
1544542 11/1967 France .
1568382 4/1968 France .
960005 6/1964 United Kingdom .

Primary Examiner—Paul J. Killos
Attorney, Agent, or Firm—Millen, White & Zelano

[57] ABSTRACT

Process for the manufacture of dialkylaminoalkyl (meth)acrylates (I) of formula:

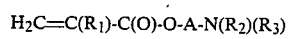

$R_1$ being a hydrogen atom or a methyl radical, A being a linear or branched alkyl radical containing 1 to 5 carbon atoms, and $R_2$ and $R_3$, which are identical or different from each other, are an alkyl radical containing 1 to 5 carbon atoms, or an aryl group, or $R_2$ and $R_3$ form a cyclic alkyl radical, in which ethyl (meth)acrylate is reacted with an aminoalcohol (II) of formula $(R_3)(R_2)N-A-OH$, A being a linear or branched alkyl radical containing 1 to 5 carbon atoms, in the presence of a polymerization inhibitor, at a temperature of between 20° and 120° C. and at a pressure equal to or lower than atmospheric pressure, in a molar ratio of ethyl (meth)acrylate to aminoalcohol (II) of between 1.5 and 5, in the presence of tetraethyl titanate, the azeotropic mixture of ethyl (meth)acrylate and ethanol is removed during the reaction, and the dialkylaminoalkyl (meth)acrylate (I) obtained is isolated at the end of reaction.

9 Claims, No Drawings

PROCESS FOR THE MANUFACTURE OF DIALKYLAMINOALKYL (METH)ACRYLATES

The present invention relates to a process for the manufacture of dialkylaminoalkyl (meth)acrylates (I) of formula

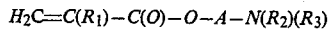

in which:

$R_1$ is a hydrogen atom or a methyl radical,

A is a linear or branched alkyl radical containing 1 to 5 carbon atoms, and $R_2$ and $R_3$, which are identical or different from each other, are an alkyl radical containing 1 to 5 carbon atoms or an aryl group, or $R_2$ and $R_3$ form a cyclic alkyl radical.

Various processes for the manufacture of (meth)acrylic esters are known.

According to British Patent 960,005, (meth)acrylic esters of formula $H_2C=CX-COOR$, R being an alkyl radical containing at least 3 carbon atoms and X being a hydrogen atom or a methyl radical, are prepared by reacting an ester $H_2C=CX-COOR'$ in which R' is an alkyl radical containing not more than 3 carbon atoms and an alcohol ROH, R having the precise meaning above, in the presence of alkyl titanate $Ti(OR'')_4$, such as tetraethyl titanate. The chief flaw of this process results from the appearance of impurities, especially of the ester $H_2C=CX-COOR''$ and the alcohol R''H which originate from the transesterification of the alkyl titanates either with the light alcohol R'OH released during the reaction, or with the higher alcohol ROH.

According to French Patent 1,544,542, acrylic esters such as dimethylaminoethyl acrylate are prepared from acrylic esters of formula $H_2C=CHCOO(CH_2)_n-CH(CH_3)_2$, in which n is equal to 0 or 1, and from alcohols, in the presence of a catalyst such as n- and isopropyl titanates, isobutyl titanates, or polybutyl titanate.

The problems due to the transesterification of the catalyst, causing the appearance of impurities in the reaction mixture and complicating the purification of the acrylic ester which is prepared are again encountered in this process.

The objective of the present invention is to remove the disadvantages of the abovementioned processes, that is to say the manufacture of dialkylaminoalkyl (meth)acrylates (I) of high purity, which are free from traces of (meth)acrylates or of alcohols with a boiling point close to that of the (meth)acrylate prepared.

More precisely, the subject of the present invention is a process for the manufacture of dialkylaminoalkyl (meth)acrylates (I) of formula:

$$H_2C=C(R_1)-C(O)-O-A-N(R_2)(R_3)$$

in which:

$R_1$ is a hydrogen atom or a methyl radical,

A is a linear or branched alkyl radical containing 1 to 5 carbon atoms, and $R_2$ and $R_3$, which are identical or different from each other, are an alkyl radical containing 1 to 5 carbon atoms, or an aryl group, or $R_2$ and $R_3$ form a cyclic alkyl radical, in which process ethyl (meth)acrylate is reacted with an aminoalcohol (II) of formula $(R_3)(R_2)N$-A-OH in which A is a linear or branched alkyl radical containing 1 to 5 carbon atoms, in the presence of at least one polymerization inhibitor, at a temperature of between 20 and 120°C. and at a pressure equal to or lower than atmospheric pressure, in a molar ratio of ethyl (meth)acrylate to aminoalcohol (II) of between 1.5 and 5, in the presence of tetraethyl titanate, the azeotropic mixture of ethyl (meth)acrylate and ethanol is removed during the reaction, and the dialkylaminoalkyl (meth)acrylate (I) obtained is isolated at the end of reaction.

The isolation of the dialkylaminoalkyl (meth)acrylate is generally carried out by distillation.

Dialkylaminoalkyl (meth)acrylate means dimethylaminoalkyl acrylate and the corresponding methacrylate.

Tetraethyl titanate is employed in a proportion of $10^{-3}$ to $5 \times 10^{-2}$ mole per mole of aminoalcohol (II), and preferably in a proportion of $5 \times 10^{-3}$ to $2 \times 10^{-2}$ mole per mole of aminoalcohol (II).

A molar ratio of ethyl (meth)acrylate to aminoalcohol (II) of between 2 and 2.5 is preferably chosen.

The temperature is preferably kept between 80 and 110°C. during the reaction.

The pressure is also preferably kept between 0.025 bar and atmospheric pressure.

Furthermore, the reaction temperature is preferably between 90 and 110°C. and the pressure is of the order of 0.5 bar to 0.8 bar.

Dimethylaminoethanol, dimethylaminopropanol, diethylaminoethanol and tert-butylaminoethanol may be mentioned among the aminoalcohols (II) suitable for the present invention.

The polymerization inhibitor employed is preferably phenothiazine, tert-butylcatechol, hydroquinone methyl ether, hydroquinone, methylene blue, copper sulfate, or iron sulfate, by itself or mixed, in an amount effective to inhibit polymerization, for example, a proportion of approximately 2,500 ppm relative to the total charge.

The process according to the invention is employed particularly for the manufacture of dimethylaminoethyl acrylate, dimethylaminopropyl acrylate, diethylaminoethyl acrylate, tert-butylaminoethyl acrylate and the corresponding methacrylates.

The present invention is advantageous in more than one way.

It permits the manufacture of dialkylaminoalkyl (meth)acrylates of high purity, which are free from alcohols and from (meth)acrylates with a boiling point in the same region.

It also involves the production of an ethyl (meth)acrylate-ethanol azeotrope free from impurities and capable of being recycled, for example in the synthesis of ethyl (meth)acrylate obtained from (meth)acrylic acid.

Furthermore, the yields (relative to the aminoalcohol (II)) of the process according to the invention are high and in most cases higher than 98%.

The examples which follow and which are given by way of guidance, will enable the invention to be better understood.

EXAMPLE 1 Manufacture of dimethylaminoethyl acrylate

The following charge (in parts by weight) is introduced into a reactor fitted with a mechanical stirring system and supporting a distillation column:

| | |
|---|---:|
| ethyl acrylate | 660 |

| | |
|---|---|
| dimethylaminoethanol | 267 |
| phenothiazine | 1,000 ppm |
| tetraethyl titanate (expressed in moles per mole of dimethylaminoethanol) | 0.005 |

The reaction is carried out at 90–95°C. and 0.53 bar. During the reaction, the ethyl acrylate-ethanol azeotrope is removed.

When the reaction is finished, the dimethylaminoethylacrylate obtained is distilled at 82°C. at 0.04 bar. 422 parts by weight of dimethylaminoethyl acrylate are collected. The yield is 98.5%.

EXAMPLE 2 Manufacture of dimethylaminoethyl methacrylate

The following charge (in parts by weight) is introduced into an apparatus identical with that employed in Example 1:

| | |
|---|---|
| ethyl methacrylate | 752 |
| dimethylaminoethanol | 267 |
| phenothiazine | 1,000 ppm |
| tetraethyl titanate (in moles per mole of dimethylaminoethanol) | 0,005 |

The reaction is carried out at 90–95°C. at 0.8 bar. The ethyl methacrylate-ethanol azeotrope is removed during the reaction.

When the reaction is finished, the dimethylaminoethyl methacrylate obtained is distilled at 94°C. at 0.04 bar. 458 parts by weight of dimethylaminoethyl methacrylate are collected. The yield is 98.5%.

EXAMPLE 3 Manufacture of diethylaminoethyl acrylate

The following charge (in parts by weight) is introduced into an apparatus identical with that employed in Example 1:

| | |
|---|---|
| ethyl acrylate | 660 |
| diethylaminoethanol | 351 |
| hydroquinone methyl ether | 1,000 ppm |
| tetraethyl titanate (in moles per mole of diethylaminoethanol) | 0.005 |

The reaction is carried out at 90–9°C. at 0.53 bar. The ethyl acrylate-ethanol azeotrope is removed during the reaction.

When the reaction is finished, the diethylaminoethyl acrylate obtained is distilled at 105°C. at 0.04 bar. 505 parts by weight thereof are collected. The yield is 98.5%.

EXAMPLE 4 Manufacture of tert-butylaminoethyl methacrylate

The following charge (in parts by weight) is introduced into an apparatus identical with that employed in Example 1:

| | |
|---|---|
| ethyl methacrylate | 752 |
| tert-butylaminoethanol | 351 |
| phenothiazine | 1,000 ppm |
| tetraethyl titanate (in moles per mole of tert-butylaminoethanol) | 0,005 |

The reaction is carried out at 90–95°C. at 0.8 bar. The ethyl methacrylate-ethanol azeotrope is removed during the reaction.

When the reaction is finished, the tert-butylaminoethyl methacrylate obtained is distilled at 118°C. at 0.04 bar. 546 parts by weight thereof are collected. The yield is 98.5%.

EXAMPLE 5 Manufacture of dimethylaminopropyl methacrylate

The following charge (in parts by weight) is introduced into an apparatus identical with that employed in Example 1:

| | |
|---|---|
| ethyl methacrylate | 752 |
| dimethylaminopropanol | 309 |
| methylene blue | 1,000 ppm |
| tetraethyl titanate (in moles per mole of dimethylaminopropanol) | 0,005 |

The reaction is carried out at 90–95°C. at 0.08 bar. The ethyl methacrylate-ethanol azeotrope is removed during the reaction.

When the reaction is finished dimethylaminopropyl methacrylate is distilled at 112°C. at 0.04 bar. 505 parts thereof are collected. The yield is 98.5%.

We claim:

1. Process for the manufacture of dialkylaminoalkyl (meth)acrylates (I) of formula:

$$H_2C=C(R_1)-C(O)-O-A-N(R_2)(R_3)$$

in which:

$R_1$ is a hydrogen atom or a methyl radical,

A is a linear or branched alkyl radical containing 1 to 5 carbon atoms, and $R_2$ and $R_3$, which are identical or different from each other, are an alkyl radical containing 1 to 5 carbon atoms, or an aryl group, or $R_2$ and $R_3$ form a cyclic alkyl radical, in which ethyl (meth)acrylate is reacted with an aminoalcohol (II) of formula $(R_3)(R_2)N$-A-OH in which A is a lin linear or branched alkyl radical containing 1 to 5 carbon atoms, in the presence of at least one polymerization inhibitor in an amount effective to inhibit polymerization, at a temperature of between 20 and 120°C. and at a pressure equal to or lower than atmospheric pressure, in a molar ratio of ethyl (meth)acrylate to aminoalcohol (II) of between 1.5 and 5, in the presence of tetraethyl titanate, the azeotropic mixture of ethyl (meth)acrylate and ethanol is removed during the reaction, and the dialkylaminoalkyl (meth)acrylate (I) obtained is isolated at the end of reaction.

2. Process as claimed in claim 1, wherein from $10^{-3}$ to $5\times10^{-2}$ mole of tetraethyl titanate per mole of aminoalcohol (II) is employed.

3. Process as claimed in claim 2, wherein $5\times10^{-3}$ to $2\times10^{-2}$ mole of tetraethyl titanate per mole of aminoalcohol (II) is employed.

4. Process as claimed in claim 1, wherein a molar ratio of ethyl (meth)acrylate to aminoalcohol (II) of between 2 and 2.5 is employed.

5. Process as claimed in claim 1, wherein the temperature is between 80 and 110°C.

6. Process as claimed in claim 1, wherein the pressure is kept between 0.025 bar and atmospheric pressure.

7. Process as claimed in claim 5, wherein the reaction temperature is between 90 and 110°C. and the pressure is of the order of 0.5 bar to 0.8 bar.

8. Process as claimed in claim 6, wherein the reaction temperature is between 90 and 110°C. and the pressure is of the order of 0.5 bar to 0.8 bar.

9. A process according to claim 1, wherein the yield, relative to the aminoalcohol (II), is higher than about 98%.

* * * * *

UNITED STATES PATENT AND TRADEMARK OFFICE
CERTIFICATE OF CORRECTION

PATENT NO. : 4,851,568

DATED : July 25, 1989

INVENTOR(S) : HURTEL ET AL

It is certified that error appears in the above-identified patent and that said Letters Patent is hereby corrected as shown below:

Title page 1, fourth inventors name:

reads "Jean-Michel Pau, Toulouse, France"

should read -- Jean-Michel Paul, Toulouse, France --

Signed and Sealed this

Twenty-second Day of May, 1990

*Attest:*

HARRY F. MANBECK, JR.

*Attesting Officer*      *Commissioner of Patents and Trademarks*